United States Patent
Prevoo et al.

(10) Patent No.: US 11,925,416 B2
(45) Date of Patent: Mar. 12, 2024

(54) METHOD OF PERFORMING AN EYE EXAMINATION TEST

(71) Applicant: EASEE HEALTH B.V., Amsterdam (NL)

(72) Inventors: Yves Franco Diano Maria Prevoo, Amsterdam (NL); Elly Onesmo Nkya, Virum (DK)

(73) Assignee: EASEE HEALTH B.V., Amsterdam (NL)

( * ) Notice: Subject to any disclaimer, the term of this patent is extended or adjusted under 35 U.S.C. 154(b) by 525 days.

(21) Appl. No.: 16/632,218

(22) PCT Filed: Jul. 20, 2018

(86) PCT No.: PCT/NL2018/050501
§ 371 (c)(1),
(2) Date: Jan. 17, 2020

(87) PCT Pub. No.: WO2019/017785
PCT Pub. Date: Jan. 24, 2019

(65) Prior Publication Data
US 2020/0253471 A1     Aug. 13, 2020

(30) Foreign Application Priority Data

Jul. 21, 2017 (NL) .............................. NL2019319

(51) Int. Cl.
*A61B 3/00* (2006.01)
*A61B 3/02* (2006.01)
(Continued)

(52) U.S. Cl.
CPC .............. *A61B 3/14* (2013.01); *A61B 3/0025* (2013.01); *A61B 3/0041* (2013.01); *A61B 3/111* (2013.01);
(Continued)

(58) Field of Classification Search
CPC ......... A61B 3/0075; A61B 3/02; A61B 3/102; A61B 3/1025; A61B 3/113; A61B 3/1015; A61B 3/1225; A61B 3/024; A61B 3/005
(Continued)

(56) References Cited

U.S. PATENT DOCUMENTS 10,799,112 B2 * 10/2020 Predham ................ A61B 3/145
2010/0092929 A1 * 4/2010 Hallowell .............. G16H 50/30
434/167

(Continued)

FOREIGN PATENT DOCUMENTS

CN       105549209 A  *  5/2016  ......... G02B 27/2214
EP       2261857 A1      12/2010

OTHER PUBLICATIONS

International Search Report for International Application No. PCT/NL2018/050501, dated Oct. 19, 2018 (3 pages).

*Primary Examiner* — Dawayne Pinkney
(74) *Attorney, Agent, or Firm* — NIXON PEABODY LLP

(57) ABSTRACT

A method of performing an eye examination test for examining eyes of a user, said method using a computing device as well as an input tool, wherein said computing device comprises a screen and comprises a camera unit arranged for capturing images, said method comprising the steps of capturing, by said camera unit of said computing device, at least one image of a human face of said user facing said screen, detecting, by said computing device, in said at least one captured image, both pupils of said human face, determining, by said computing device, a distance of said user to said screen based on a predetermined distance between pupils of a user, a distance between said detected pupils in said at least one captured image, and a focal length of said camera unit corresponding to said at least one captured (Continued)

image, and performing, by said computing device in combination with said input tool, said eye examination test using said determined distance.

10 Claims, 2 Drawing Sheets

(51) Int. Cl.
*A61B 3/10* (2006.01)
*A61B 3/11* (2006.01)
*A61B 3/12* (2006.01)
*A61B 3/14* (2006.01)
*G06V 40/16* (2022.01)
*G06V 40/18* (2022.01)
*H04N 23/54* (2023.01)
*H04N 23/67* (2023.01)

(52) U.S. Cl.
CPC .......... *G06V 40/171* (2022.01); *G06V 40/193* (2022.01); *H04N 23/54* (2023.01); *H04N 23/67* (2023.01)

(58) Field of Classification Search
USPC .............. 351/208, 200, 205, 206, 209, 210, 351/221–223, 245–246
See application file for complete search history.

(56) References Cited

U.S. PATENT DOCUMENTS

| | | | |
|---|---|---|---|
| 2014/0347456 A1* | 11/2014 | Kato | H04N 13/332 348/59 |
| 2014/0372139 A1* | 12/2014 | Tasso | A61F 2/145 705/2 |
| 2017/0112378 A1 | 4/2017 | Tamkin | |
| 2019/0295507 A1* | 9/2019 | Abuelsaad | A61B 3/111 |

* cited by examiner

METHOD OF PERFORMING AN EYE EXAMINATION TEST

CROSS-REFERENCE TO RELATED APPLICATIONS

This application is a U.S. National Stage Entry of International Application No. PCT/NL2018/050501, filed Jul. 20, 2018, which claims priority to Netherlands Application No. NL2019319, filed Jul. 21, 2017, the contents of which are herein incorporated by reference in their entirety.

The present disclosure is directed to a method of performing an eye examination test. More specifically, the present disclosure is directed to an eye examination test using a computing device as well as a User Equipment.

An eye examination test is, typically, a series of tests performed by a professional, for example an optician, an ophthalmologist or anything alike. An eye examination test may be used for testing the visual acuity, pupil function, extraocular muscle motility, ophthalmoscopty through an undilated pupil, amongst other things. The assessment of the refractive state of the eye may also be an important part of ophthalmic and optometric clinical practice. Such eye examination tests may also be used to detect potentially treatable blinding eye diseases, ocular manifestations of systemic disease, or signs of tumours or other anomalies of the brain.

Conventionally, a user needs to visit an optician, or ophthalmologist, to examine his/her eyes. Several tools may be required to examine the eyes of the user. The optician, or ophthalmologist, then performs some eye examination tests and adjusts the tests based on input he/she receives from the user. In the end, the optician, or ophthalmologist is able to provide a conclusion related to the eyes based on the tests that were performed.

In the last couple of years, online eye examination tests have been developed. As such, a user no longer needs to physically visit an optician, or ophthalmologist, but is able to perform the eye examination test online. The development of an unsupervised online subjective refraction method makes a refraction more accessible and may be quite cost-saving.

A known method of performing an eye examination test uses a computing device as well as a User Equipment. The computing device comprises a screen for displaying all kinds of eye examination test related visualizations. The User Equipment, for example a mobile phone, is used as an input tool. The user provides its input on questionnaires displayed on the screen using the User Equipment.

In order for the eye examination test to be performed accurately, it may be required that the user is placed in front of the screen at a distance of about three metres. The user is guided to this distance using the shoe size of the user. That is, the user needs to input his/her shoe size into the online eye examination test. Based on the inputted shoe size, the total amount of heel-toe steps are calculated. For example, for a shoe size 10, about 10 heel-toe steps are required to get to the above mentioned three metres distance. The user is then requested to perform 10 heel-toe steps to assure that the user is at about three metres distance from the screen.

Finally, the eye examination test is performed using the computing device and using the User Equipment as some sort of remote control for the computing device.

One of the drawbacks of the known eye examination test as disclosed above is that the results may not be accurate as it is difficult to determine that the user is actually at the desired three metres distance during the eye examination test. It is merely trusted that the user has performed the procedure of the heel-toe steps correctly to get to this distance.

SUMMARY OF THE DISCLOSURE

It is an object of the present disclosure to achieve an eye examination test in which the distance of the user to the screen can be more reliably assessed such that the results of the eye examination test are more accurate.

To better address one or more of the concerns of the prior art, in a first aspect of the disclosure, there is provided a method of performing an eye examination test for examining eyes of a user. The method uses a computing device as well as a input tool, such as a mobile User Equipment, UE, wherein said computing device comprises a screen and comprises a camera unit arranged for capturing images.

The method comprising the steps of:
  capturing, by said camera unit of said computing device, at least one image of a human face of said user facing said screen;
  detecting, by said computing device, in said at least one captured image, both pupils of said human face;
  determining, by said computing device, a distance of said user to said screen based on:
    a predetermined distance between pupils of a user;
    a distance between said detected pupils in said at least one captured image, and
    a focal length corresponding to said at least one captured image;
  performing, by said computing device in combination with said UE, said eye examination test using said determined distance.

It was one of the insights of the inventors that the pupillary distance of people, i.e. the predetermined distance between pupils of a user, is generally about constant. Therefore, that parameter may be used for determining the distance of the user to the screen.

The inventors furthermore noticed that the type of camera unit used for capturing the at least one image may influence the eye examination test, because the focal length varies per type of camera unit and/or per captured image. It was an insight of the inventors to control for this variable by determining the focal length of the camera corresponding to the at least one captured image prior to the step of determining the distance of the user to the screen.

Following the above, at least three parameters should be taken into account in order to accurately determine the actual distance of the user to the screen.

The first parameter is the above described generally constant distance between pupils of a user. A second parameter is the distance between the pupils in the at least one captured image. This distance is, for example, expressed in pixels. Finally, the focal length of the camera unit used for capturing the image is used for converting the distance between the pupils in the captured image to an actual measure for the physical distance of the user to the screen.

In accordance with the present disclosure, the input tool is, for example, a mobile UE separated from the computing device. The mobile UE may be any of a smart phone, tablet, smart watch or anything alike. Such a mobile UE may be used, by the user, as an input device for inputting answers to questionnaires displayed on the screen. It is noted that, during the eye examination test, the user is at a particular distance from the computing device such that the user is not able to physically reach the computing device. The mobile UE is thus used as an extended input device. As another option, the input tool may be a microphone. The microphone may be comprised by the computing device. Answers to specific questionnaires may then be provided using voice recognition algorithms running on the computing device. Thus the input tool is to be carried by the user under examination during the test.

In accordance with the present disclosure, the computing device may be any of a desktop computer, a tablet, a laptop, or anything alike. For example, such a computing device will run an internet browser which supports the eye examination test as disclosed.

In the above, it is assumed that the distance of the camera unit to the screen is negligible, or known beforehand. Following the method as presented, the distance of the user to the camera unit is calculated, while the distance between the screen and the user is actually the parameter that is decisive. The distance of the user to the camera unit is roughly the same as the distance of the user to the screen in case of a webcam that is integrated in the screen. In other scenario's, the calculated distance may be corrected for using a known distance between the camera unit and the screen.

Examples according to the present disclosure are described in the following.

In an example according to the first aspect of the present disclosure said method comprises the step of:
 determining, by said computing device, said focal length of said camera unit by any of:
  retrieving said focal length in meta data of said captured at least one image;
  calculating said focal length based on said predetermined distance between pupils of a user and a predetermined initial distance of a user facing said screen.

The focal length of the camera unit used for capturing said at least one image may be determined in several ways. As a first option, it was noted that many types of camera units log the used focal length in meta data of the image that was captured. As such, the meta data belonging to the captured image comprises the focal length required for determining the distance of the user to the screen.

It was also noted that some camera units do not log such a focal length. It is then not possible to obtain this variable from the meta data of the captured image. In such a case, the focal length of the camera unit used during capturing of the image may be calculated based on the predetermined distance between pupils of a user and a predetermined initial distance of a user facing the screen. It was found that a user sits at a distance of about 40-70 cm from his/her screen when normally operating the computing device. In the initial image captured by the camera unit, it is declared that the distance of the user to the screen is that 40-70 cm. This information may be used for determining the focal length of the camera unit.

Following the above, an advantage of this example is that a focal length corresponding to the camera unit may be determined, even if such a focal length is not known beforehand.

In an example according to the first aspect of the present disclosure said eye examination test is to be performed with a predefined distance of said user to said screen, and wherein said method further comprises:
 providing said user, by said computing device using said screen, feedback on said distance based on said measured distance and said predefined distance of said user to said screen.

With a predefined distance of said user to said screen is meant a distance between said user and said screen at which said eye examination test should be performed. In other words, said user should stand at a predefined distance from said screen. Said predefined distance is then compared with said determined distance of said user to said screen. Thereafter said user is provided with feedback on whether he/she should further approach said screen or whether he/she should move away from said screen.

An advantage of this example is that said user can position him/herself at said predefined distance, such that said eye examination test can be accurately performed.

In an example according to the first aspect of the present disclosure said predetermined distance between pupils of any user is between 55 mm-70 mm, preferably between 60 mm-65 mm, even more preferably around 63 mm.

An advantage of this example is that a relatively accurate determination can be made with respect to said distance of said user to said screen. This may be advantages for eye examination tests that are being performed to calculate the refractive properties of the eye, as such a calculation is relatively sensitive to errors.

In an example according to the first aspect of the present disclosure said predetermined initial distance of a user facing said screen is between 30 cm-80 cm, preferably between 40 cm-70 cm, even more preferably around 65 cm.

In an example according to the first aspect of the present disclosure, said predetermined initial distance of a user facing said screen is determined based on a plurality of reference images, wherein said reference images are images from previous eye examination tests that are stored in a database accessible by said server.

An advantage of this example is that said predetermined initial distance can be more accurately determined such that said eye examination test can be more accurately performed.

With a predetermined initial distance of a user is meant a distance, wherein said user is normally operating said computing device. For example, the computing device resides on a desk, and the user is sitting at that desk. In such a case, it is found that the distance between the user and the screen is, typically, approximately 50 cm.

An advantage of this example is that it is possible to relatively quickly determine the focal length of said camera unit used during capturing an initial image. To determine said focal length, the initial image is created by said camera prior to said eye examination test, wherein said user is at said predetermined initial distance. Said focal length can then be determined based on said predetermined initial distance of said user to said screen, said predetermined distance between pupils of a user and a distance between said detected pupils in said initial image.

In an example according to the first aspect of the present disclosure said method further comprises the step of:
 detecting, by said computing device, in said captured at least one image, using a facial feature algorithm, a facial feature of said user facing said screen,
 and wherein said step of performing said eye examination test uses said detected facial feature.

A facial feature is, for example, squinting, closing or covering a left and/or right eye, or tilting his/her head, smiling, a pupil size, etc.

The facial features may be detected by comparing the captured image with a plurality of reference images, wherein the reference images comprise one of more of said facial features.

An advantage of this example is that the facial feature can be taken into account when analysing the user's eye sight.

In an example according to the first aspect of the present disclosure said method comprises the steps of:
- providing, by said computing device, said at least one captured image to a central database corresponding to a central server;
- correlating, by said central server, images in said central database with images of human faces having predefined facial features;
- amending, by said central server, said facial feature algorithm based on said correlating;
- providing, by said central server, said updated facial feature algorithm to said computing device.

An advantage of this example is that said facial features can be relatively accurately assessed. By correlating said at least one captured image with images of human faces having predefined facial features, it is possible determine differences between the images. Based on these differences, it is possible to determine if an eye examination test is performed correctly. For example, when a user is squinting his/her eyes for during eye examination, this can be taken into account analysing the results of the eye examination test.

In an example according to the first aspect of the present disclosure said method further comprises the step of:
- detecting in said captured at least one image an environmental feature in said image, wherein said step of performing said eye examination test uses said environmental feature.

Said environmental feature is, for example, an amount of light in an area wherein said image is captured.

An advantage of this example is that said environmental feature can be taken into account when analysing said user's eye sight.

In a second aspect of the present disclosure a system for performing an eye examination test for examining eyes of a user, said system comprising a computing device as well as a mobile User Equipment, UE, said computing device comprising:
- a camera unit arranged for capturing at least one image of a human face of a user facing a screen comprised by said computing device;
- a detect unit arranged for detecting, in said captured at least one image, both pupils of said human face;
- process equipment arranged for determining a distance of said user to said screen based on:
  - a predetermined distance between pupils of any user;
  - a distance between said detected pupils in said captured at least one image, and
  - a focal length of said camera unit;
- wherein said computing device and said UE comprise eye examination test means arranged for performing said eye examination test using said determined distance between of said user to said screen.

In accordance with the present disclosure, different aspects applicable to the above mentioned examples of the methods, including the advantages thereof, correspond to the aspects which are applicable to the system according to the present disclosure.

In an example of the second aspect of the present disclosure said computing device further comprises:
- a focal length determination unit arranged for determining said focal length of said camera unit by any of:
  - retrieving said focal length in meta data of said captured at least one image;
  - calculating said focal length based on said predetermined distance between pupils of any user and a predetermined initial distance of a user facing said screen.

An advantage of this example is that a focal length corresponding to the specific camera is used. Thereby, it is possible to control for the type of camera.

In an example of the second aspect of the present disclosure said eye examination test is to be performed with a predefined distance of said user to said screen, and wherein said computing device further comprises:
- provide equipment arranged for providing said user, using said screen, feedback on said distance based on said measured distance and said predefined distance of said user to said screen.

Said provide equipment comprises means to communicate with said user, for example, via text or audio.

An advantage of this example is that said user can position him/herself at said predetermined distance, such that said eye examination test can be accurately performed.

In an example of the second aspect of the present disclosure said predetermined distance between pupils of any user is between 55 mm-70 mm, preferably between 60 mm-65 mm, even more preferably around 63 mm.

An advantage of this example is that a relatively accurate determination can be made about said distance of said user to said screen.

In an example of the second aspect of the present disclosure said predetermined initial distance of a user facing said screen is between 30 cm-80 cm, preferably between 40 cm-70 cm, even more preferably around 65 cm.

In an example of the second aspect of the present disclosure said system further comprises:
- detect equipment arranged for detecting, in said captured at least one image, using a facial feature algorithm, a facial feature of said user facing said screen,
- and wherein said eye examination test means use said detected facial feature.

An advantage of this example is that the facial feature can be taken into account when analysing the user's eye sight.

In an example of the second aspect of the present disclosure said system further comprises a central server having a central database, wherein said computing device comprises:
- transmit equipment arranged for providing said at least one captured image to said central database;
- wherein said central server comprises:
- correlate equipment arranged for correlating images in said central database with images of human faces having predefined facial features;
- amend equipment arranged for amending said facial feature algorithm based on said correlating;
- provide equipment arranged for providing said updated facial feature algorithm to said computing device.

An advantage of this example is that said facial features can be relatively accurately assessed. By correlating said at least one captured image with images of human faces having predefined facial features, it is possible determine differences between the images. Based on these differences, it is possible to determine if an eye examination test is performed correctly.

The expressions, i.e. the wording, of the different aspects comprised by the method and system according to the present disclosure should not be taken literally. The wording of the aspects is merely chosen to accurately express the rationale behind the actual functioning of the aspects.

The above-mentioned and other features and advantages of the disclosure will be best understood from the following description referring to the attached drawings. In the drawings, like reference numerals denote identical parts or parts performing an identical or comparable function or operation.

DETAILED DESCRIPTION OF THE DRAWINGS

Figure 1:
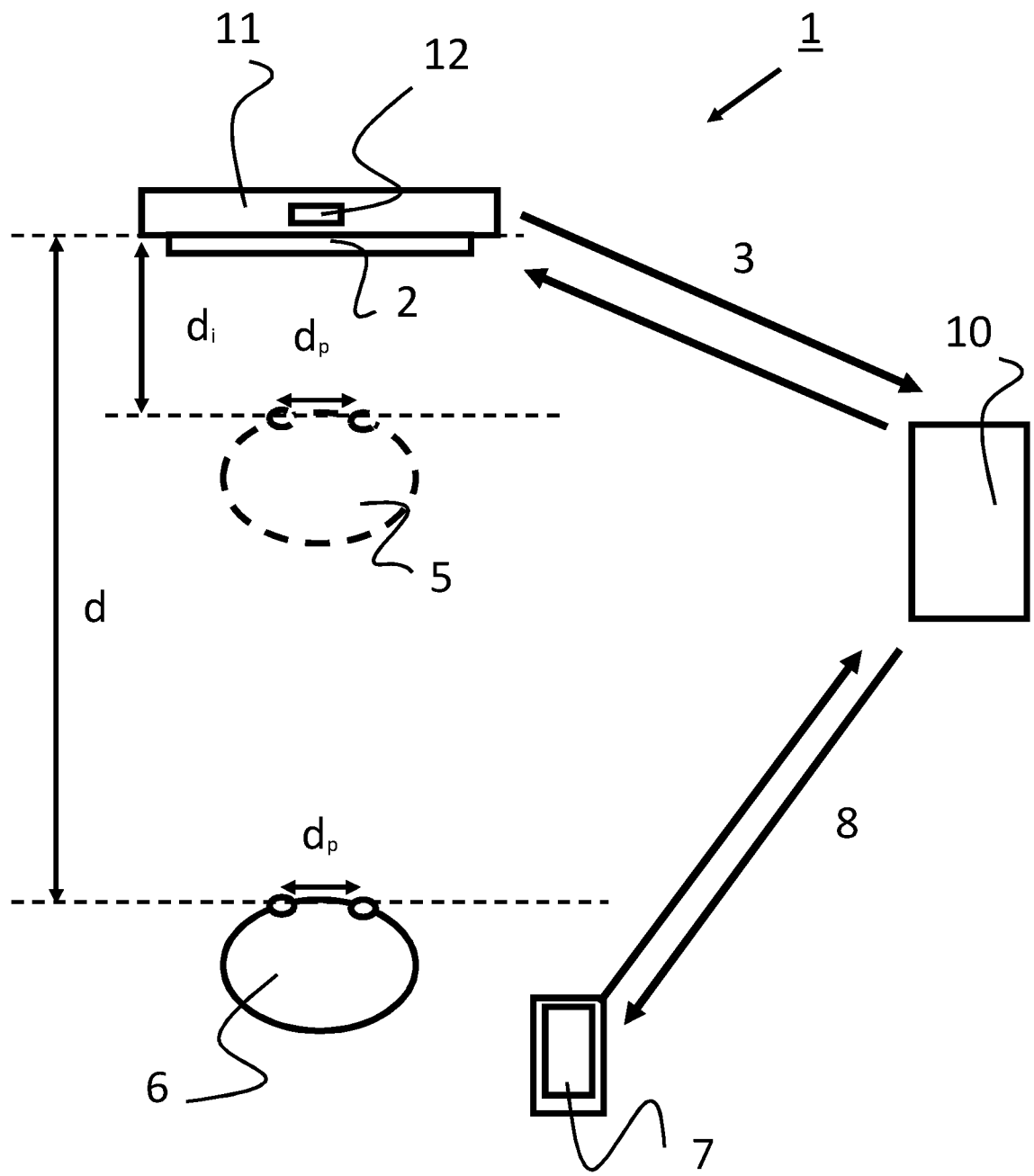
FIG. 1 discloses the basic concept of the invention in accordance with the present disclosure.

FIG. 1 discloses the basic concept of the invention in accordance with the present disclosure. More specifically, FIG. 1 discloses, in a conceptual manner, a measurement setup 1 used during the method of performing the eye examination test.

Here, the measurement setup 1 comprises a computing device 11, a mobile User Equipment 7 as well as a central server 10.

The computing device 11 comprises a screen 2, which screen 2 is used for displaying all kinds of visualizations that are used by the eye examination test for examining the eyes of a user. For example, the visualizations may comprise a plurality of letters, signs, characters, etc. These visualizations are, subsequently, provided in different sizes. A user then needs to provide input on the things he/she is able to observe on the screen. That is, the user needs to input the visualizations that he/she is able to recognize on the screen. The results of the eye examination test depend on the input that is provided by the user.

The distance d between the user 6 and the screen 2 should be determined and should be taken into account during the eye examination test in order to provide for accurate results. The present disclosure is directed to a method for obtaining that particular distance d.

The distance d is calculated based on images taken by a camera unit, for example a webcam 12. The webcam 12 is comprised by the computing unit 11. Typically, a webcam 12 is placed just above the screen 2 such that the distance between the webcam 12 and the user is approximately the same.

The distance d is determined as follows. First, it was recognized that the pupillary distance $d_p$ of any user is roughly constant, and should be used as a first parameter in calculating the distance. More specifically, the pupillary distance $d_p$ is about 55-70 mm, even more specifically between 60 mm-65 mm, even more specifically 63 mm. This parameter is taken into account during the calculation of the distance d between the user 6 and the screen 2.

In another example, the user may input its own pupillary distance $d_p$ into the eye examination test. The calculation of the distance d is then performed based on the inputted distance $d_p$ by the user in stead of the predetermined distance between pupils of a user. Such an inputted distance is more accurate compared to a standard, predefined, average distance between pupils of a user.

A second parameter is related to the distance between the detected pupils in the at least one captured image. As such, in a first step, the pupils of the user need to be detected, in the captured image, by the computing device. The distance between the pupils in the image may then be measured once the pupils have been detected. The measured distance between the pupils may be expressed in centimetres, pixels or any other distance measure. Very specifically, the measured distance between the pupils in the captured image may, for example, be 0.6 mm.

A third parameter is related to the focal length of the camera unit 12 corresponding to the at least one captured image. The focal length may be required to correctly interpret the ratio between the actual distance $d_p$ between the pupils of a user and the measured distance $\tilde{d}_p$ between the pupils of a user.

The focal length may be obtained in a variety of manners which is elaborated in more detail here below.

The focal length may be determined by retrieving the focal length in meta data of the captured at least one image. That is, each image may be stored along with meta data, wherein the meta data related to the setting of the camera unit during the capturing of that particular image. The meta data may, for example, comprise resolution settings, ISO settings, diaphragm settings, but also the focal length of the camera unit.

Another option is that the focal length is calculated based on the predetermined distance between pupils of a user and a predetermined initial distance of a user facing the screen. The initial distance is shown in FIG. 1 and is referenced to using $d_i$. The distance $d_i$ may relate to an initial distance that a user sits in front of the screen 2. Typically, the computing device 11 resides on a desk, and the user 5, at least initially, sits at that particular desk. It is found that the distance between the face of a user, i.e. the pupils of the user, and the screen 2 is, generally, about constant for each user, and for each type of desk. The distance is, roughly, between 30 cm-80 cm, most likely between 40 cm-70 cm, even more likely around 65 cm. Such an initial distance is then taken into account when calculating the focal length of the camera unit 12.

The focal length is then calculated using the predetermined initial distance of a user facing the screen, said distance between said detected pupils in said at least one captured image, and said predetermined distance between pupils. The focal length can then be determined with the formulas:

$$1/f = 1/o + 1/i \text{ and } M = i/o = II/OO$$

Wherein f=focal length;
o=the initial distance to the user;
i=a distance between the image and the user;
M=magnification
II=the distance between the user's pupils in the image; and
OO=the predetermined distance between pupils.

The inventors have found that the eye examination test may be improved even further in case the eye examination test takes into account facial features of the user facing the screen. The facial features may indicate whether the user is trying hard to read something, i.e. the user is squinting, may indicate which eye the user has covered during the eye examination test, or anything alike.

As such, the computing device may be arranged to detect a facial feature of the user facing the screen, and may perform the eye examination test using that detected facial feature. In order to do so, the computing device may use a facial feature algorithm, which is explained in more detail here below.

In a first step, the computing device may provide 3 the at least one captured image to a central database corresponding to a central server 10. The facial feature algorithm, as identified here above, may be run at the central server 10. The central server 10 may correlate the received captured image with a plurality of images in its database, wherein each of that plurality of images has a certain facial feature present. That is, some of those plurality of images may comprise a human face in which one of the eyes is covered. Other of those plurality of images may comprise a human face in which the user is squinting, etc. By correlating the received captured image with those images in the database, it can be assessed whether the user 6 is squinting, tilting his/her head, covering a particular eye, etc.

Figure 2:
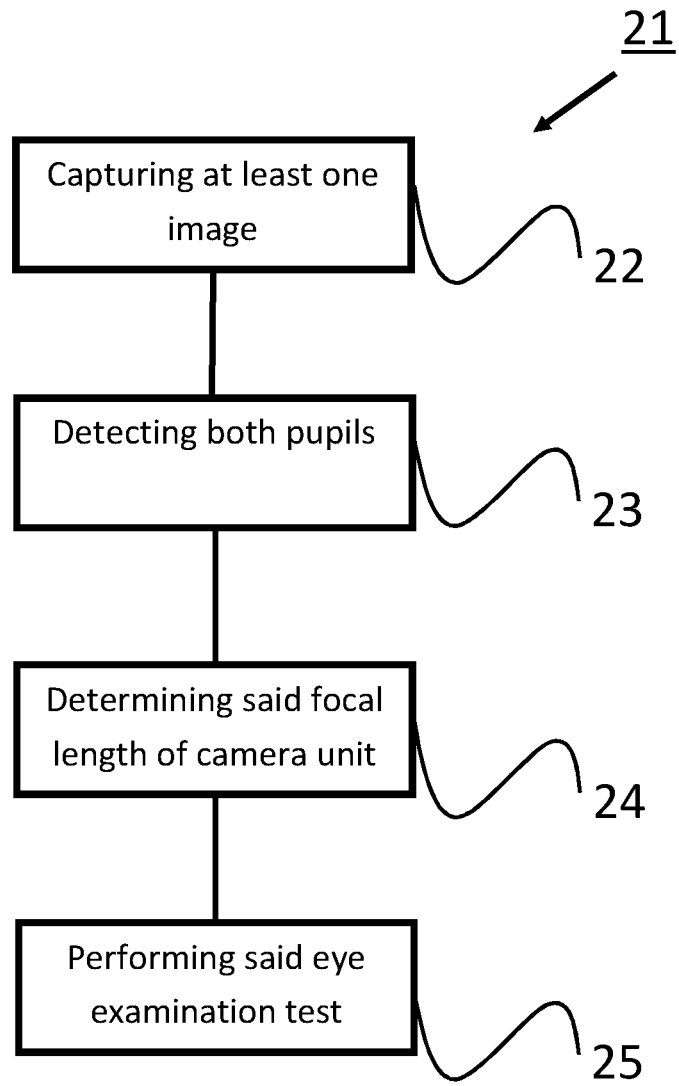
FIG. 2 discloses an example of a method in accordance with the present disclosure.

It is noted that the algorithms to determine the distance of the user to the screen as well as the algorithms to determine the facial features and/or the environment features are typically executed, i.e. performed, by the computing device. The related captured images may be provided to a central server for improvement purposes. That is, the central server may use these captured images to improve the algorithms. The updated algorithms may then be used by the computing device in subsequent captured images. FIG. 2 discloses an example of a method 21 in accordance with the present disclosure.

The method is directed to performing an eye examination test for examining eyes of a user, said method using a computing device as well as a mobile User Equipment, UE, wherein said computing device comprises a screen and comprises a camera unit arranged for capturing images.

The method comprising the steps of:
capturing 22, by said camera unit of said computing device, at least one image of a human face of said user facing said screen;
detecting 23, by said computing device, in said at least one captured image, both pupils of said human face;
determining 24, by said computing device, a distance of said user to said screen based on:
a predetermined distance between pupils of a user;
a distance between said detected pupils in said at least one captured image, and
a focal length of said camera unit corresponding to said at least one captured image;
performing 25, by said computing device in combination with said UE, said eye examination test using said determined distance.

Following the description above it is noted that one of the advantages of the present disclosure is that the distance between the user and the screen can be determined, which distance is taken into account during the eye examination test. This improves the accuracy of the eye examination test.

Following the description above it is noted that another advantage of the present disclosure is that the eye examination test may be performed more quickly as it reduces the time to setup, i.e. the time to get the user to a predetermined distance from the screen.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope thereof.

The invention claimed is:

1. A method of performing an eye examination test for examining at least a visual acuity of eyes of a user, said method using a computing device as well as an input tool, wherein said computing device comprises a screen and comprises a camera unit arranged for capturing images, said method comprising:
capturing, by said camera unit of said computing device, at least one image of a human face of said user facing said screen;
detecting, by said computing device, in said at least one captured image, both pupils of said human face;
determining, by said computing device, a distance of said user to said screen based on:
a predetermined distance between pupils of a user;
a distance between said detected pupils in said at least one captured image, and
a focal length of said camera unit corresponding to said at least one captured image, wherein said focal length of said camera unit is determined by calculating said focal length based on said predetermined distance between pupils of a user, a predetermined initial distance of a user facing said screen, and said distance between said detected pupils in said at least one captured image;
wherein said predetermined initial distance of a user facing said screen is between 30 cm-70 cm;
performing, by said computing device in combination with said input tool, said eye examination test using said determined distance between the user and the screen, the user using the input tool for inputting answers to questionnaires displayed on the screen.

2. The method in accordance with claim 1, wherein said eye examination test is to be performed with a predefined distance of said user to said screen, and wherein said method further comprises:
providing said user, by said computing device using said screen, feedback on said distance based on said measured distance and said predefined distance of said user to said screen.

3. The method in accordance with claim 1, wherein said predetermined distance between pupils of any user is between 55 mm-70 mm.

4. The method in accordance with claim 1, wherein said method further comprises:
detecting, by said computing device, in said captured at least one image, using a facial feature algorithm, a facial feature of said user facing said screen,
and wherein said step of performing said eye examination test uses said detected facial feature.

5. The method in accordance with claim 4, wherein said method comprises:
providing, by said computing device, said at least one captured image to a central database corresponding to a central server;
correlating, by said central server, images in said central database with images of human faces having predefined facial features;
amending, by said central server, said facial feature algorithm based on said correlating;
providing, by said central server, said updated facial feature algorithm to said computing device.

6. A system for performing an eye examination test for examining at least a visual acuity of eyes of a user, said system comprising a computing device as well as an input tool, said computing device comprising:

a camera unit arranged for capturing at least one image of a human face of a user facing a screen comprised by said computing device;

a detect unit arranged for detecting, in said at least one captured image, both pupils of said human face;

process equipment arranged for determining a distance of said user to said screen based on:

a predetermined distance between pupils of any user;

a distance between said detected pupils in said captured at least one image, and a focal length of said camera unit;

wherein said computing device further comprises:

a focal length determination unit arranged for determining said focal length of said camera unit by calculating said focal length based on said predetermined distance between pupils of any user, a predetermined initial distance of a user facing said screen, and said distance between said detected pupils in said at least one captured image;

wherein said predetermined initial distance of a user facing said screen is between 30 cm and 70 cm;

wherein said computing device and said input tool comprise eye examination test means arranged for performing said eye examination test using said determined distance between said user and said screen, the user using the input tool for inputting answers to questionnaires displayed on the screen.

7. The system in accordance with claim 6, wherein said eye examination test is to be performed with a predefined distance of said user to said screen, and wherein said computing device further comprises:

provide equipment arranged for providing said user, using said screen, feedback on said distance based on said measured distance and said predefined distance of said user to said screen.

8. The system in accordance with claim 6, wherein said predetermined distance between pupils of any user is between 55 mm-70 mm.

9. The system in accordance with claim 6, wherein said system further comprises:

detect equipment arranged for detecting, in said captured at least one image, using a facial feature algorithm, a facial feature of said user facing said screen, and wherein said eye examination test means use said detected facial feature.

10. The system in accordance with claim 6, wherein said system further comprises a central server having a central database, wherein said computing device comprises:

transmit equipment arranged for providing said at least one captured image to said central database;

wherein said central server comprises:

correlate equipment arranged for correlating images in said central database with images of human faces having predefined facial features;

amend equipment arranged for amending said facial feature algorithm based on said correlating;

provide equipment arranged for providing said updated facial feature algorithm to said computing device.

\* \* \* \* \*